United States Patent [19]

Mori

[11] Patent Number: 4,703,719

[45] Date of Patent: * Nov. 3, 1987

[54] FISH FEEDING DEVICE

[76] Inventor: Kei Mori, 3-16-3-501, Kaminoge, Setagaya, Tokyo, Japan

[*] Notice: The portion of the term of this patent subsequent to Oct. 13, 2004 has been disclaimed.

[21] Appl. No.: 797,370

[22] Filed: Nov. 12, 1985

[30] Foreign Application Priority Data

Nov. 15, 1984 [JP] Japan ................................ 59-241409

[51] Int. Cl.⁴ ............................................. A01K 61/00
[52] U.S. Cl. ........................................ 119/3; 47/1.4
[58] Field of Search .............. 119/3; 47/1.4; 126/425, 126/440; 405/70, 220, 195, 219, 211, 218, 221, 224, 21, 23, 24, 25, 26, 27, 28, 29, 30, 32, 33, 34, 35, 63, 64, 71, 201, 202, 203, 204, 210, 209, 60

[56] References Cited

U.S. PATENT DOCUMENTS

| | | | |
|---|---|---|---|
| 1,859,322 | 5/1932 | Wilson | 114/256 |
| 2,565,369 | 8/1951 | Hamilton | 114/226 |
| 2,709,984 | 6/1955 | Marks | 119/3 |
| 3,283,515 | 11/1966 | Pottorf | 405/211 |
| 3,785,313 | 1/1974 | Rosenberg | 114/266 |
| 3,802,673 | 4/1974 | Ross | 114/264 X |
| 3,841,266 | 10/1974 | Hoshino | 119/2 |
| 3,951,104 | 4/1976 | Neff | 119/3 |
| 3,955,317 | 5/1976 | Gudin | 47/1.4 X |
| 4,086,161 | 4/1978 | Burton | 47/1.4 X |
| 4,142,816 | 3/1979 | Kramer | 405/27 X |
| 4,265,625 | 6/1980 | Muller-Feuga | 119/2 |
| 4,279,538 | 7/1981 | Bossa | 405/70 |
| 4,324,067 | 4/1982 | Kessler | 47/1.4 |
| 4,340,812 | 7/1982 | Mori | 126/425 |
| 4,365,576 | 12/1982 | Cook | 405/205 X |
| 4,447,718 | 5/1984 | Mori | 126/425 X |
| 4,459,643 | 7/1984 | Mori | 362/32 |
| 4,501,084 | 2/1985 | Mori | 43/17.5 |
| 4,536,988 | 8/1985 | Hogen | 47/1.4 |

FOREIGN PATENT DOCUMENTS

| | | | |
|---|---|---|---|
| 1126039 | 6/1982 | Canada | 405/27 |
| 0080414 | 6/1983 | European Pat. Off. | 119/3 |
| EP85926 | 8/1983 | European Pat. Off. | 47/1.4 |
| 1299164 | 7/1969 | Fed. Rep. of Germany | 47/1.4 |
| 2560245 | 8/1985 | France | 405/63 |
| 61241 | 4/1985 | Japan | 47/1.4 |
| 105444 | 6/1985 | Japan | 47/1.4 |
| 1083944 | 4/1984 | U.S.S.R. | 47/1.4 |

*Primary Examiner*—Robert A. Hafer
*Assistant Examiner*—Danton DeMille
*Attorney, Agent, or Firm*—Jordan and Hamburg

[57] ABSTRACT

A fish feeding device utilizing a solar ray collecting device and a algae cultivating device. The fish feeding device comprises cylinders vertically installed in water so as to waft or float therein, solar ray collecting devices and/or artificial light sources equipped on the cylinders, cultivation devices suspended from the cylinders for cultivating algae or the like, and optical conductors for supplying solar rays and/or artificial light rays to the cultivation devices.

11 Claims, 3 Drawing Figures

FISH FEEDING DEVICE

BACKGROUND OF THE INVENTION

The present invention relates to a fish feeding device, in particular, a fish feeding device effectively utilizing a solar ray collecting device and algae cultivating device.

The present applicant has previously proposed various ways to focus solar rays or artificial light rays by use of lenses or the like, to guide the same into an optical conductor cable, and thereby to transmit them onto an optional desired place through the optical conductor cable. The solar rays or the artificial light rays transmitted and emitted in such a way are employed for photosynthesis and for use in illuminating or for other like purposes, for example, to promote the cultivation of plants or to cultivate the algae or the like.

And further, the present applicant has already proposed various cultivation devices for cultivating algae or the like, for instance, chlorela. Basically, the cultivation of chlorella needs light rays and carbon dioxide $CO_2$ required for the photo synthesis. When the light rays and the carbon dioxide $CO_2$ are supplied to a chlorella cultivating tub, the chlorella is cultivated and at the same time oxygen $O_2$ is created.

As mentioned above, the solar rays or the artificial light rays are focused by use of lenses or the like and guided into the optical conductor. The light rays are further guided through the optical conductor into the chlorella cultivating tub, and radiated therein from the optical conductor in order to supply the light rays to objects to be cultivated. As for the carbon dioxide $CO_2$, generally an in-bombe-packed carbon dioxide $CO_2$ available in the market place is provided for the chlorella cultivating tub.

The chlorella created as mentioned before is employed as bait for feeding fish. However, it has not yet been tried to equip the chlorella cultivating device as mentioned above directly in water for the purpose of feeding fish.

SUMMARY OF THE INVENTION

It is an object of the present invention to provide a fish feeding device utilizing a solar ray collecting device and a algae cultivating device.

It is another object of the present invention to provide a fish feeding device possible to install in water so as to waft therein.

It is another object of the present invention to provide a fish feeding device possible to improve the water quality of the sea, lake, or pond, etc.

It is another object of the present invention to provide a fish feeding device which does not apt to be affected by the fluctuation of tidal wave.

It is another object of the present invention to provide a fish feeding device which can be easily moved to the other place by means of a ship or possible to change the place for feeding the fish.

The above-mentioned features and other advantages of the present invention will be apparent from the following detailed description which goes with the accompanying drawings.

DESCRIPTION OF THE PREFERRED EMBODIMENT

Figure 1:
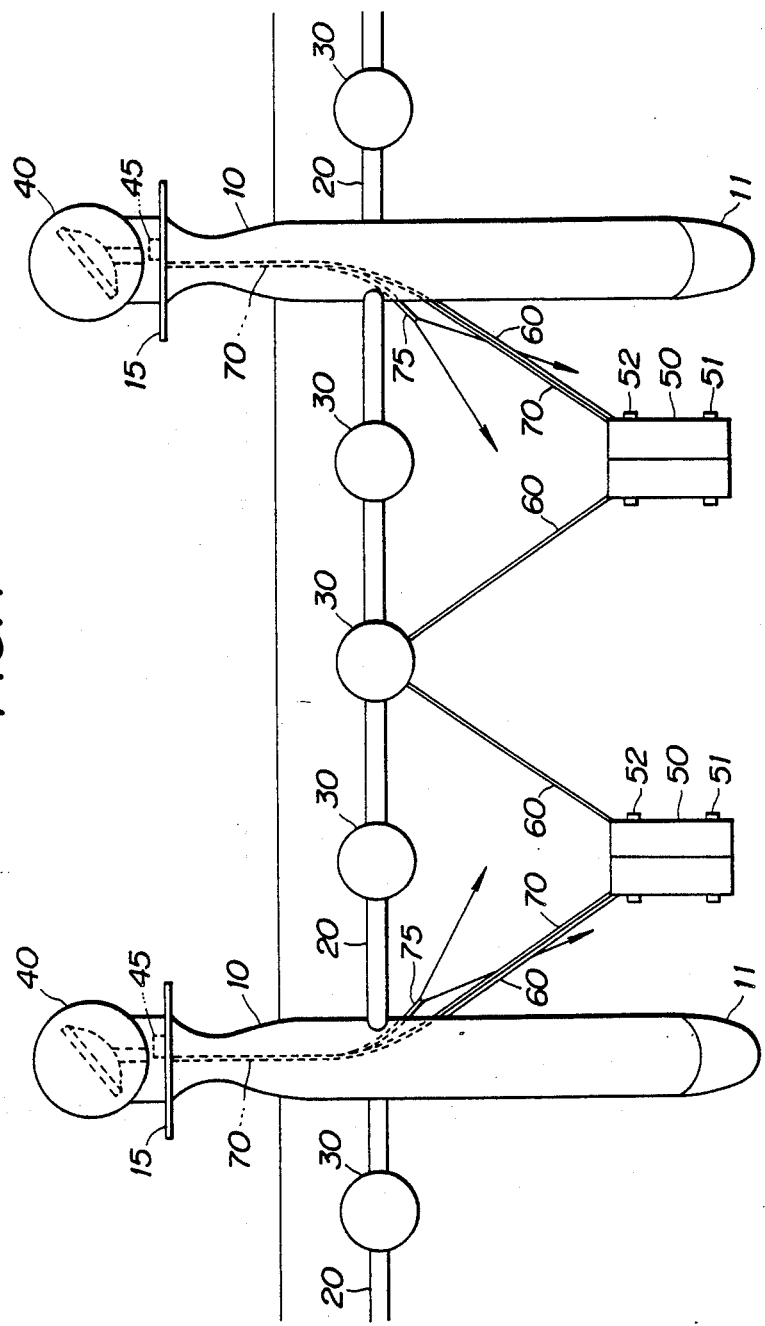
FIG. 1 is a partial side view of the construction for explaining an embodiment of a fish feeding device according to the present invention.

FIG. 1 is a partial side view of the construction for explaining an embodiment of a fish feeding device according to the present invention. In FIG. 1, 10 is a cylinder vertically installed in water so as to waft or float therein, 11 a weight member attached to the lower end portion of the wafting cylinder 10, 15 a water separating plate, 20 a connection arm for connecting the wafting cylinder with the others, 30 a connection knot put between the connection arms, 40 a solar ray collecting device equipped on the wafting cylinder 10, 45 an artificial light source device powered by a electric generator or a solar battery, 50 a cultivation device for cultivating the algae or the like, for instance, chlorella, 60 a wire and/or a cylinder for suspending the chlorella cultivating device 50 from the wafting cylinder, and 70 an optical conductor cable installed along the wire or through the cylinder.

As is well known, the solar ray collecting device 40 focuses the solar rays by use of the lenses or the like and guides the same into the optical conductor cable. In such a manner, the light rays guided into the optical conductor cable are supplied through the optical conductor cable to the chlorella cultivating device 50. The light rays are employed therein as a photo synthesis light source for cultivating the chlorella.

Furthermore, an artificial light source portion 45 activated by a solar battery, a storage battery charged by the solar battery, and/or an electric generator is equipped in the fish feeding device. The light rays emitted from the artificial light source are supplied through the optical conductor cable 70 to the chlorella cultivating device. Even when the solar rays are weak in the intensity thereof or when the solar rays can not be collected during the night time, it will be possible to cultivate the chlorella in such a manner.

And further, if the outer circumferential surface of the chlorella cultivating device 50 is constructed with the transparent substance, the light rays employed for cultivating the chlorella leak from the chlorella cultivating device. Not only gather the fish around the chlorella cultivating device seeking the light rays which leak therefrom, but also the algae stick on the outer circumferential surface of the chlorella cultivating device seeking the same.

The algae or chlorella is a bait for the fish. By eating the algae the fish grow up. At the same time, the outer circumferential surface of the chlorella cultivating tub is cleaned completely. Moreover, the optical conductor cables 75 are installed for radiating a part of the solar rays or the artificial light rays focused in such a manner as mentioned above. When the light rays are radiated from the upper portion of the chlorella cultivating device by use of the optical conductor cable 75, the fish gather around the device seeking the light rays. In such a manner, it will be possible to effectively collect the fish.

And further, each chlorella cultivating device which has previously proposed by the present applicant in the Japanese Patent Application No. 59-165123/1984 has a taking-in inlet 51 for taking in water existing outside thereof and a discharging outlet 52 for discharging the cultivated chlorella and/or the oxygen $O_2$ created by the cultivation of chlorella. The carbon dioxide $CO_2$, phosphorus, nitrogen, nutritious salt contained or melted in water are taken in through the inlet 51 into the chlorella cultivating device 50 together with water in order to cultivate the chlorella. The cultivated chlorella and/or the oxygen $O_2$ created by the cultivation of chlorella are discharged into water through the outlet 52.

Consequently, since the substance needed for the cultivation of chlorella is taken in from water and the oxygen $O_2$ and the bait needed for feeding the fish are created in the chlorella cultivating device 50 and returned them into the sea water in such a manner, it follows that the fish-feeding can be performed at a lower cost and effectively improving the quality of water.

Figure 2:
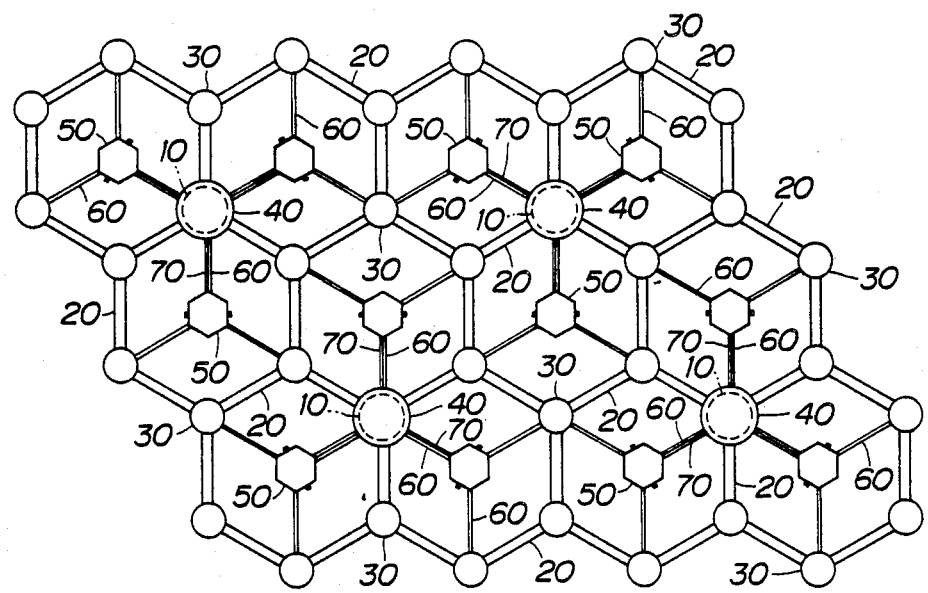
FIG. 2 is a plan view for explaining a construction thereof.

FIG. 2 is a plan view for explaining a construction of the fish breeding device according to the present invention. As shown in FIG. 2, the wafting cylinder 10 and the connection knots 30 are adjacently arranged respectively so as to form respective vertexes of a hexagon. The wafting cylinder 10 and the connection knot 30 are connected with each other by use of the connection arm 20.

The respective cultivation devices 50 are suspended from the wafting cylinder 10 and the connection knots 30 by use of the wire 60. The greater part of the solar rays collected by the solar ray collecting device 40 and/or the light rays emitted from the artificial light source device 45 is supplied through the optical conductor cable 70 to the respective cultivation devices 50. For instance, those light rays are employed as the photo synthesis light source for cultivating the chlorella and a part of the light rays is radiated into water through the optical conductor cable 75 in order to illuminate the chlorella cultivating device and its neighboring area.

The connection arm 20, and the connection knot 30, etc. are constructed as a rigid body. And further, supposing that the connection arm and the connection knot are constructed with a hollow body and a full or partial portion of the wall surface thereof is constructed with a transparent substance, the state of the chlorella cultivating device in the water and other parts can be observed through the wall surface of the hollow body.

In the case of the embodiment shown in FIG. 2, one solar ray collecting device supplies the light rays to three cultivation devices. However, the invention is not limited to the embodiment shown in FIG. 2, since such number can be changed optionally in accordance with the scale of the solar ray collecting device and the cultivation device.

Figure 3:
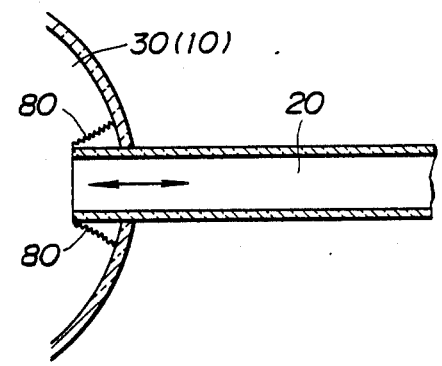
FIG. 3 is a cross-sectional view of the main part showing an embodiment of the connecting construction for connecting the connection knot 30 or the wafting object with the connection arm.

FIG. 3 is a cross-sectional view of the main part showing an embodiment of the connecting construction for connecting the connection knot 30 or the wafting cylinder 10 with the connection arm 20. In FIG. 3, 80 is a resilient partition member for connecting the end portion of the connection arm 20 with the connection knot 30 or the wafting cylinder 10. In such a construction, when the entire portion of the fish feeding device moves horizontally the partition member expands and contracts so that the connection arm 20 deviates in a direction as shown by the double-head arrow. In consequence, the partition member 80 can effectively absorb the variation of its location.

As is apparent from the foregoing description, according to the present invention, it is possible to feed the fish effectively improving the water quality of sea, lakes, or ponds, etc. And further, according to the present invention, the cylinder is installed in water so as to waft therein, and therefore the same deviates easily up and down and does not easily deviate laterally. Consequently, the cylinder is not apt to be affected by the fluctuation of tidal waves and the solar ray collecting device can effectively collect the solar rays as is the case when it is fixed on an underground place. Therefore, it is not necessary to provide a regulating device such as a stabilizer. Furthermore, since the entire portion of the device is disposed in water so as to waft therein, it can be easily moved to other places by means of a ship or the like. In consequence, it is possible to change easily the place for feeding the fish.

I claim:

1. A floatable fish feeding device comprising a plurality of elongated cylindrical bodies disposed in a body of water, said elongated cylindrical bodies having longitudinal axes which are vertically disposed as said cylindrical bodies float in said body of water, connecting arms connecting said cylindrical bodies to form a floating interconnected structure, cultivating devices within said body of water for cultivating algae, suspension means suspending said cultivating device from said structure, said suspension means suspending said cultivating device within said body of water, said cultivating device having inlet means for taking in carbon dioxide phosphorus, nitrogen and salt from said body of water, said cultivating device having outlet means for discharging algae and oxygen into said body of water, solar ray collecting means mounted on and disposed over said structure, and optical cable means for transmitting light ray from said solar ray collecting means to said cultivating device, said structure floating in said body of water to rise and lower with the changing tide.

2. A floatable fish feeding device according to claim 1 wherein said cylindrical bodies extend above the structure and above the level of said body of water, said solar ray colelcting means being disposed on said cylindrical bodies about said body of water.

3. A floatable fish feeding device according to claim 1 wherein at least some of said optical conductor cable means radiate light into the body of water surrounding said cultivating device to illuminate said cultivating device.

4. A floatable fish feeding device according to claim 1 wherein said cultivating device comprises an outer wall of transparent material through which light is radiated to the body of water outside said cultivating device for cultivating algae on the outside of said cultivating device.

5. A floatable fish feeding device according to claim 1 further comprising a water separation plate means on said cylindrical bodies at an elevation below said solar ray collecting means.

6. A floatable fish feeding plant comprising a plurality of elongated cylindrical bodies each having a longitudinal axis, each of said cylindrical bodies having vertically disposed within a body of water, a plurality of connecting arms each having a longitudinal axis, connecting knot means at the ends of at least some of said connecting arms, each of said connecting arms being horizontally disposed and being connected to said connecting knot means and to said cylindrical bodies to form an interconnected structure floatable within a body of water, said connecting arms being formed in the configuration of a plurality of interconnected hexagons with at least one connecting arm of each hexagon being common with at least one connecting arm of another hexagon, each of said hexagons having angled corners, said cylindrical bodies and said connecting knot means being located at said angled corners, a culture device for cultivating algae, suspension means for suspending said culture device from said structure such that said culture device is disposed within said body of water, solar ray collecting means mounted on said structure for collecting solar rays, said solar ray collecting means being disposed above said body of water, optical conductor cable means on said structure for transmitting the collected solar rays from said solar ray collecting means to said culture device for cultivating algae, said culture device thereby cultivating said algae utilizing said transmitted solar rays as a photosynthesis light source, said culture device having inlet means for taking in carbon dioxide, phosphorus, nitrogen, and nitritious salt contained in said body of water, said culture device having outlet means for discharging said algae cultivated by said culture device into said body of water for the feeding of fish, said outlet means also discharging oxygen into said body of water.

7. A floatable fish feeding plant according to claim 6 wherein said connecting arms and connecting knot means are hollow and have transparent portions to provide for viewing the culture device through said transparent portions.

8. A floatable fish feeding plant according to claim 6 wherein each of said hexagonal configurations defines a centrally disposed area which is substantially in the center of each of said hexagonals, each of said centrally disposed areas having one of said culture devices disposed thereat.

9. A floatable fish feeding device according to claim 6 further comprising a resilient partition member for connecting the ends of said connecting arms to said cylindrical bodies and to said connecting knot means such that said resilient means provides for resilient relative movement between the connecting knot means and the connecting arm means and cylindrical bodies.

10. A floatable fish feeding plant according to claim 6 wherein said connecting arms and said connecting knot means are hollow to provide a passage therein.

11. A floatable fish feeding plant according to claim 10 wherein said connecting arms and said connecting knot means are at least partially formed of a transparent material.

* * * * *